(12) United States Patent
Murakami et al.

(10) Patent No.: US 7,218,394 B2
(45) Date of Patent: May 15, 2007

(54) LIQUID SPECIMEN ANALYSIS DISK ASSEMBLY

(75) Inventors: Kenji Murakami, Toyo (JP);
Masakazu Mori, Saijo (JP); Hiroyuki Hamamoto, Imabari (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 484 days.

(21) Appl. No.: 10/901,438

(22) Filed: Jul. 29, 2004

(65) Prior Publication Data

US 2006/0023208 A1    Feb. 2, 2006

(51) Int. Cl.
*G01N 1/10* (2006.01)
*G01N 35/00* (2006.01)

(52) U.S. Cl. .................................. 356/246; 436/45
(58) Field of Classification Search ............... 356/246; 436/45
See application file for complete search history.

(56) References Cited

U.S. PATENT DOCUMENTS

| 4,284,602 A | * | 8/1981 | Kelton et al. ............... 422/72 |
| 4,687,638 A | * | 8/1987 | Benajam ..................... 422/73 |
| 4,756,883 A | * | 7/1988 | Romanauskas .............. 422/72 |
| 5,256,376 A | * | 10/1993 | Callan et al. ............... 422/102 |
| 2003/0035352 A1 | * | 2/2003 | Worthington ............ 369/47.35 |
| 2005/0087479 A1 | * | 4/2005 | Okada et al. ............... 210/94 |
| 2005/0176059 A1 | * | 8/2005 | Pal et al. ..................... 435/7.1 |

FOREIGN PATENT DOCUMENTS

WO    WO 00/26677    5/2000

* cited by examiner

*Primary Examiner*—Gregory J. Toatley, Jr.
*Assistant Examiner*—Bryan Giglio
(74) *Attorney, Agent, or Firm*—Steptoe & Johnson LLP

(57) ABSTRACT

The present invention provides a liquid specimen analysis disk assembly, which prevents a liquid specimen from adhering onto a surface of a disk and leaking out of the disk, and is easy to handle during injection of the specimen. The disk assembly includes a guide member detachably provided on the disk and having a guide hole for guiding a distal portion of a specimen injector toward a specimen injection port, so that the specimen is injected into a specimen spreading cavity or an internal channel from the specimen injection port and rotated about an axis of the disk, and the specimen spread in the channel following the rotation is optically scanned for analyzing. The distal portion of the specimen injector is inserted into the guide hole and assuredly guided to the center of the specimen injection port, thus preventing the specimen from adhering onto the disk surface around the injection port.

23 Claims, 16 Drawing Sheets

LIQUID SPECIMEN ANALYSIS DISK ASSEMBLY

FIELD OF THE INVENTION

The present invention relates to a liquid specimen analysis disk assembly which includes a liquid specimen analysis disk to be optically scanned for analyzing a liquid specimen injected into a specimen spreading cavity thereof from a specimen injection port provided in a front surface thereof and spread in the specimen spreading cavity by rotating the disk about an axis of the disk. Particularly, the invention relates to liquid specimen analysis disk assembly which provides easy handling and safety for the injection of the specimen.

BACKGROUND OF THE INVENTION

There has been proposed an analyzer which is adapted to qualitatively and quantitatively analyzing a specimen spread in a disk. The analyzer is employed for analysis of a blood specimen for diagnosis of a disease.

As shown in FIG. 18, a specimen analysis disk 320 to be used in an analyzer of this type has tracks (not shown) engraved thereon like a conventional optical disk, and includes specimen injection ports 325 and specimen spreading cavities 322 provided therein in communication with the respective specimen injection ports 325. After specimens are respectively injected into the specimen spreading cavities 322, the disk 320 is rotated to spread the specimens in the respective specimen spreading cavities 322. Then, the specimens spread in the respective specimen spreading cavities 322 are simultaneously detected by a focus/tracking technique with the use of a focus/tracking system commonly employed in an optical disk device such as a CD-ROM device (see, for example, WO00/026677).

However, biological specimens such as blood specimens which may possibly be contaminated with infectious pathogens are often analyzed with the use of the disk. If such a specimen is leaked and scattered out of the disk 320 in the analysis and an operator touches the leaked specimen, there is a possibility that the operator is infected with a pathogen. For prevention of the leakage of the specimen, a sealing sheet (not shown) is manually applied onto the specimen injection port 325 after the injection of the specimen.

However, the manual application of the sealing sheet reduces handling ease. In addition, the sealing sheet is liable to be displaced from a due position, failing to assuredly seal the specimen injection port 325. Where the specimen adheres to the periphery of the specimen injection port 325 in the injection of the specimen, there is a possibility that the operator touches the specimen when the sealing sheet is applied onto the specimen injection port 325. Particularly, where the disk 320 has a small thickness, the specimen injection ports do not have a sufficiently great depth. Hence, there is a risk that the specimen adheres to the periphery of the specimen injection port 325 with a distal portion of a specimen injector being displaced from the specimen injection port 325. Therefore, the operator is required to perform the specimen injecting operation very carefully.

DISCLOSURE OF THE INVENTION

To solve the aforesaid problem, it is an object of the present invention to provide a liquid specimen analysis disk assembly, which prevents a liquid specimen from adhering onto a surface of a disk and leaking out of the disk, and provides handling ease for injection of the specimen.

According to an inventive aspect as set forth in claim 1 to achieve the aforesaid object, there is provided a liquid specimen analysis disk assembly, which comprises: a liquid specimen analysis disk to be optically scanned for analyzing a liquid specimen therein, the liquid specimen analysis disk having a specimen injection port for injecting the liquid specimen into a specimen spreading cavity in which the liquid specimen is spread by rotating the disk about an axis of the disk; and a guide member detachably provided on the disk and having a guide hole for guiding a distal portion of a specimen injector toward the specimen injection port for the injection of the liquid specimen. With this arrangement, the distal portion of the specimen injector is inserted into the guide hole thereby to be assuredly guided to the center of the specimen injection port. Thus, the liquid specimen is prevented from adhering onto the disk surface around the specimen injection port.

According to an inventive aspect as set forth in claim 2, the guide hole of the guide member is tapered so that one end opening thereof opposed to the specimen injection port has a smaller diameter than the other end opening thereof facing away from the specimen injection port in the liquid specimen analysis disk assembly according to claim 1. With this arrangement, the conical distal portion of the specimen injector can easily and assuredly be guided to the center of the specimen injection port along the interior surface of the guide hole.

According to an inventive aspect as set forth in claim 3, the guide hole of the guide member has an inner diameter such as to be fitted around a part of the distal portion of the specimen injector in the liquid specimen analysis disk assembly according to claim 1. With this arrangement, the insertion depth of the conical distal portion of the specimen injector can be limited by the guide hole. Thus, the distal end of the specimen injector can be positioned intermediate between a lower surface of the guide member and a bottom of the specimen injection port thereby to be prevented from contacting the bottom of the specimen injection port.

According to an inventive aspect as set forth in claim 4, the one end opening of the guide hole opposed to the specimen injection port has a smaller inner diameter than the specimen injection port in the liquid specimen analysis disk assembly according to claim 1. With this arrangement, the distal portion of the specimen injector can easily and assuredly be guided to the center of the specimen injection port.

According to an inventive aspect as set forth in claim 5, the guide member has a tubular projection surrounding the one end opening of the guide hole opposed to the specimen injection port in the liquid specimen analysis disk assembly according to claim 1. Even if the specimen ejected from the distal end of the specimen injector adheres onto the interior surface of the guide hole, the specimen never spreads out of the tubular projection. Therefore, the specimen adhesion area can be minimized.

According to an inventive aspect as set forth in claim 6, the tubular projection has a distal end having an outer diameter smaller than the inner diameter of the specimen injection port in the liquid specimen analysis disk assembly according to claim 5. Even if the specimen adhering onto the interior surface of the guide hole drips, the specimen drips from the lower end of the tubular projection into the specimen injection port. Thus, the specimen is prevented from adhering onto the disk surface around the specimen injection port.

According to an inventive aspect as set forth in claim 7, the guide member is constituted by a lid of a disk case in the liquid specimen analysis disk assembly according to claim 1. With the lid of the disk case being closed, the specimen is injected into the specimen spreading cavity through the guide hole and the specimen injection port. After completion of the injection of the specimen, the lid is opened, and the specimen injection port is sealed. Then, the disk is taken out of the disk case. Since the guide member is constituted by the lid of the conventionally used disk case, the number of the components can be reduced. The guide member (lid) can be separated from the liquid specimen analysis disk when the disk is taken out of the disk case. Hence, there is no need to separately perform a guide member detaching operation.

According to an inventive aspect as set forth in claim 8, the liquid specimen analysis disk assembly according to claim 1 further comprises a cover member provided on the guide member for opening and closing the guide hole. Even if the specimen ejected from the distal end of the specimen injector adheres onto the interior surface of the guide hole, the operator is prevented from touching the specimen by the cover member which covers the guide hole after the injection of the specimen.

According to an inventive aspect as set forth in claim 9, the cover member is pivotal parallel to the surface of the disk about a pivot axis on the lid of the disk case in the liquid specimen analysis disk assembly according to claim 8. This arrangement obviates the need to provide a space for the opening and closing of the cover member.

According to an inventive aspect as set forth in claim 10, the cover member has an engagement member which is brought into engagement with an engagement member provided on the lid of the disk case, when the cover member is pivoted to cover the specimen injection port, to prevent the cover member from pivoting in a reverse direction in the liquid specimen analysis disk assembly according to claim 9. This arrangement prevents the operator from inadvertently opening the cover member after the injection of the specimen and touching the specimen.

According to an inventive aspect as set forth in claim 11, the liquid specimen analysis disk assembly according to claim 7 further comprises an adhesive sealing sheet which is retained in a folded state or in a rolled state between the disk and the lid of the disk case and extended for sealing the specimen injection port, and a tab provided integrally with the adhesive sealing sheet as extending out of the disk case. After the completion of the injection of the specimen, the tab is pulled to extend the adhesive sealing sheet, whereby the adhesive sealing sheet is applied onto a portion of the disk surface including the specimen injection port. With this arrangement, the operator is prevented from touching the specimen when opening the lid and taking the disk out of the disk case.

According to an inventive aspect as set forth in claim 12, the tab is constituted by a part of a releasable sheet which lines the adhesive sealing sheet in the liquid specimen analysis disk assembly according to claim 11. By pulling the tab, the adhesive sealing sheet is smoothly extended to be applied onto the disk surface portion including the specimen injection port. Thus, the handling ease can be improved.

According to an inventive aspect as set forth in claim 13, the liquid specimen analysis disk assembly according to claim 11 further comprises a roller member coupled with the tab for pressing the extended adhesive sealing sheet against the disk surface. The roller member is operated to press the adhesive sealing sheet against the disk surface, while the adhesive sealing sheet is extended by pulling the tab or after completion of the extension of the adhesive sealing sheet. Thus, the adhesive sealing sheet can more firmly be applied onto the disk surface.

According to an inventive aspect as set forth in claim 14, the lid is overlapped with a case body of the disk case, and the lid and the case body each have an opening formed in an overlapped portion thereof for extracting the tab out of the disk case in the liquid specimen analysis disk assembly according to claim 11. The lid cannot be opened until the tab is removed through the opening of the disk case, in other words, until the specimen injection port is completely sealed with the adhesive sealing sheet after the injection of the specimen. This arrangement prevents the operator from inadvertently opening the lid before the completion of the sealing of the specimen injection port and touching the specimen.

According to an inventive aspect as set forth in claim 15, there is provided a liquid specimen analysis disk assembly, which comprises: a liquid specimen analysis disk to be optically scanned for analyzing a liquid specimen therein, the liquid specimen analysis disk having a specimen injection port provided in a front surface thereof for injecting the liquid specimen into a specimen spreading cavity in which the liquid specimen is spread by rotating the disk about an axis of the disk, the liquid specimen analysis disk having a groove formed in the surface of the disk provided with the specimen injection port; and a seal member slidable in engagement with the groove for sealing the specimen injection port. With this arrangement, the specimen injection port can be sealed with the seal member immediately after completion of the injection of the specimen, so that the operator is prevented from touching the specimen.

According to an inventive aspect as set forth in claim 16, the seal member and the groove respectively have engagement members which are brought into engagement with each other, when the seal member is slid to seal the specimen injection port, to prevent the seal member from sliding in a reverse direction in the liquid specimen analysis disk assembly according to claim 15. Thus, the operator is prevented from inadvertently sliding the seal member to open the specimen injection port after the injection of the specimen.

According to an inventive aspect as set forth in claim 17, there is provided a liquid specimen analysis disk assembly, which comprises: a liquid specimen analysis disk to be optically scanned for analyzing liquid specimens therein, the liquid specimen analysis disk having a plurality of specimen injection ports provided in a front surface thereof for injecting the liquid specimens into specimen spreading cavities in which the liquid specimens are respectively spread by rotating the disk about an axis of the disk; and a temporary seal retaining member detachably provided on the disk and having plural adhesive sealing sheets temporarily retained at predetermined positions thereon, the adhesive sealing sheets being each covered with a releasable sheet. The temporary seal retaining member is positioned in opposed relation to the surface of the disk, and the releasable sheets are removed from the adhesive sealing sheets. Then, the adhesive sealing sheets are pressed against the disk surface. Thus, the plural specimen injection ports can speedily individually be sealed with the adhesive sealing sheets.

According to an inventive aspect as set forth in claim 18, the temporary seal retaining member is partly or entirely composed of a resilient material in the liquid specimen analysis disk assembly according to claim 17. With this arrangement, the adhesive sealing sheets can be pressed with a uniform pressure for the application thereof. Thus, the specimen injection ports can assuredly be sealed.

According to an inventive aspect as set forth in claim 19, first identification marks having different characters are provided in association with the respective specimen injection ports, and second identification marks having characters corresponding to the characters of the first identification marks are respectively provided on the adhesive sealing sheets or the releasable sheets associated with the respective specimen injection ports, or on the temporary seal retaining member in the vicinity of the respective adhesive sealing sheets in the liquid specimen analysis disk assembly according to claim 17. With this arrangement, the correspondences between the specimen injection ports and the adhesive sealing sheets can easily visually be identified, thereby preventing the operator from removing a wrong releasable sheet.

According to an inventive aspect as set forth in claim 20, the temporary seal retaining member is pivotal about a pivot axis of a hinge provided in a disk case in the liquid specimen analysis disk assembly according to claim 17. With this arrangement, the temporary seal retaining member is already positioned with respect to the disk. Therefore, the specimen injection ports can individually speedily be sealed with the corresponding adhesive sealing sheets by removing the corresponding releasable sheets and pivoting the temporary seal retaining member about the pivot axis of the hinge.

According to an inventive aspect as set forth in claim 21, the temporary seal retaining member is constituted by a lid of the disk case in the liquid specimen analysis disk assembly according to claim 20. With this arrangement, the specimen injection ports can individually speedily be sealed with the corresponding seal members by removing the corresponding releasable sheets and closing the lid.

According to an inventive aspect as set forth in claim 22, there is provided a liquid specimen analysis disk assembly, which comprises: a liquid specimen analysis disk to be optically scanned for analyzing liquid specimens therein, the liquid specimen analysis disk having a plurality of specimen injection ports provided in a front surface thereof for injecting the liquid specimens into specimen spreading cavities in which the liquid specimens are respectively spread by rotating the disk about an axis of the disk; and a guide member having plural introduction members provided in association with the respective specimen injection ports and linked to one another, the introduction members each having a guide hole for guiding a distal portion of a specimen injector toward the specimen injection port for the injection of the liquid specimen. With this arrangement, the introduction members each guide the distal portion of the specimen injector into the specimen injection port, whereby the specimen can assuredly be injected into each of the specimen spreading cavities.

According to an inventive aspect as set forth in claim 23, the introduction members each have a truncated cone shape, and the guide hole includes an upper guide hole portion and a lower guide hole portion for guiding the distal portion of the specimen injector in the liquid specimen analysis disk assembly according to claim 22. With this arrangement, the distal portion of the specimen injector can smoothly be guided from the upper guide hole portion to the lower guide hole portion, whereby the specimen can assuredly be injected into each of the specimen spreading cavities.

DESCRIPTION OF THE PREFERRED EMBODIMENTS

Embodiments of the present invention will hereinafter be described with reference to the attached drawings.

(Embodiment 1)

Figure 1:
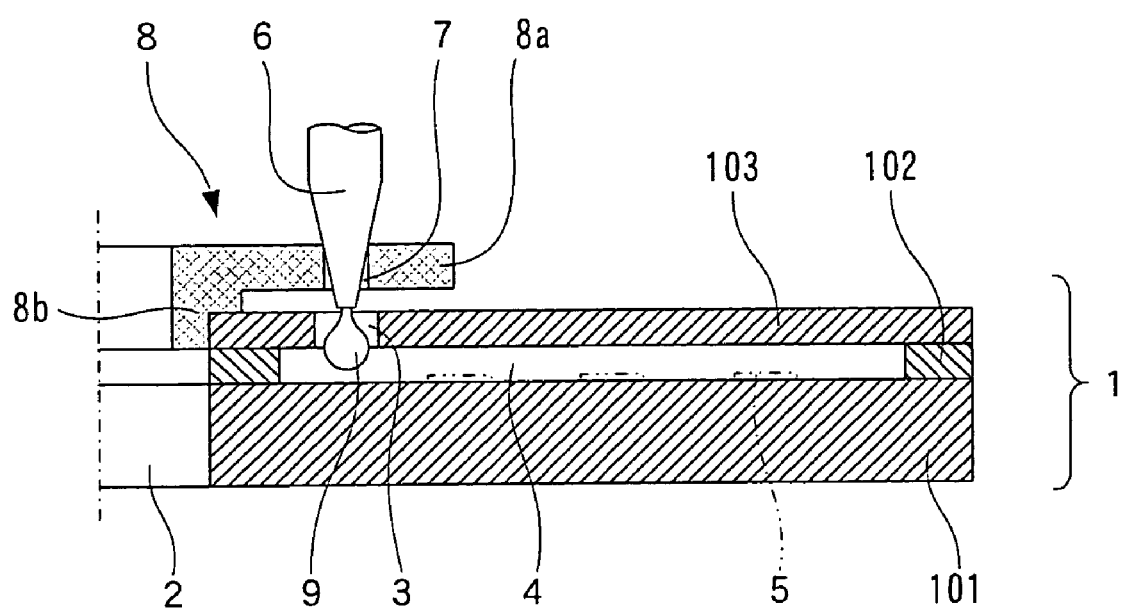
FIG. 1 is an enlarged vertical sectional view illustrating a part of a liquid specimen analysis disk assembly according to Embodiment 1 of the present invention.
Figure 2:
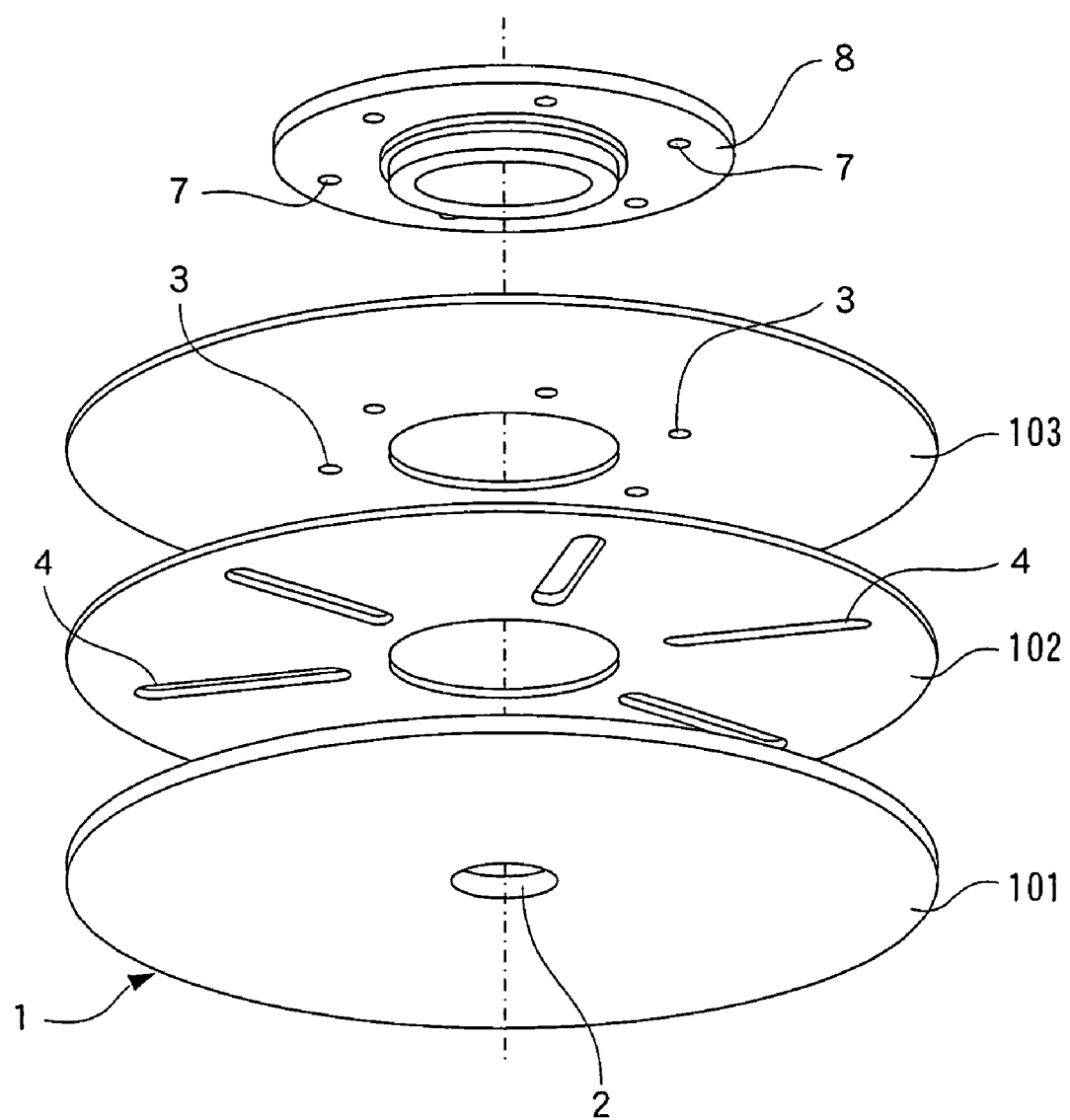
FIG. 2 is an exploded perspective view of the liquid specimen analysis disk assembly of FIG. 1.

FIG. 1 is an enlarged vertical sectional view illustrating a part of a liquid specimen analysis disk assembly according to Embodiment 1 of the present invention, and FIG. 2 is an exploded perspective view of the liquid specimen analysis disk assembly. This liquid specimen analysis disk assembly is related to claim 1.

Figure 18:
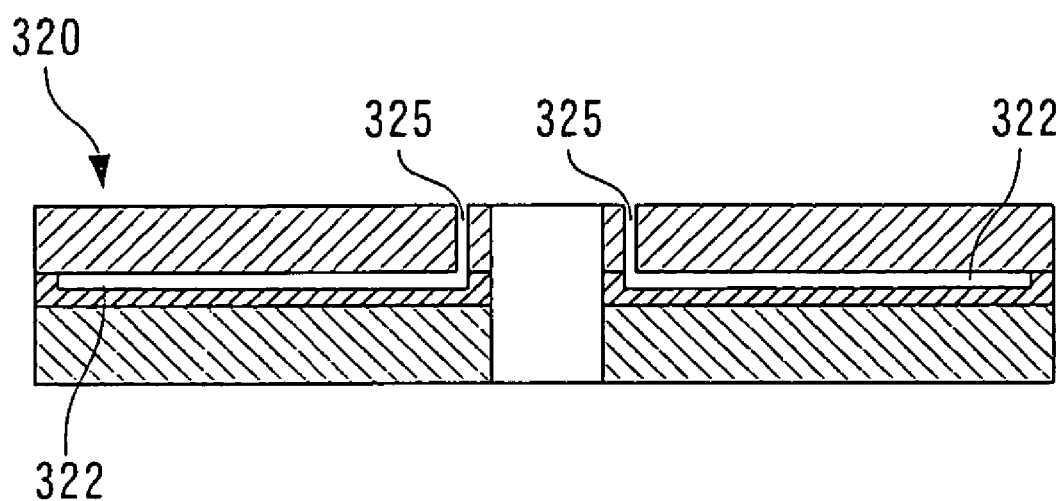
FIG. 18 is a vertical sectional view of a conventional liquid specimen analysis disk.

As shown in FIGS. 1 and 2, the liquid specimen analysis disk assembly includes a disk 1 having substantially the same construction as the conventional disk described with reference to FIG. 18. The disk 1 has a disk shape as a whole, and includes a plurality of specimen injection ports 3 provided in a front surface thereof around a center hole 2, and channels 4 provided therein in communication with the respective specimen injection ports 3 as extending radially from the respective specimen injection ports 3.

The disk 1 has a three-tier structure including a first plate (disk substrate) 101, a second plate (disk adhesion tier) 102 and a third plate (disk cover) 103 laminated in this order.

The first plate 101 defines bottom faces of the channels 4, and is composed of polycarbonate or glass having an optically uniform refractivity. The first plate 101 is of a round shape, and has a center hole formed in its center.

The second plate 102 has six slits extending radially and each defining the contour of the channel 4, and includes a base such as a PET film and adhesive layers provided on opposite surfaces of the base.

The third plate 103 defines top faces of the channels 4. The six specimen injection ports 3 are provided equiangularly around a center hole of the third plate 103 as extending thicknesswise through the third plate 103 in association with radially innermost ends of the channels 4. Though not shown, a reflective film such as of gold, silver or aluminum is provided on the third plate 103 for detection of a light beam by a conventional focus detection technique such as an astigmatic method or a knife edge method, and a spiral groove or concentric grooves are provided on the third plate 103 for scanning the light beam at a minute constant pitch.

As indicated by phantom lines, a reagent 5 may be provided in the channels 4 by application thereof, for example. The reagent reacts with a component of a liquid specimen such as a biological specimen (e.g., blood or urine) to be analyzed, and a change in optical characteristics (e.g., transmittance, color or the like) of the reagent is detected for determination of the presence of the component or for determination of the concentration or quantity of the component. Depending on the analysis, the reagent is preliminarily added to the specimen, or the reagent is not required (e.g., when the analysis is performed for determination of the number of blood cells). In this case, the reagent 5 is not provided in the channels 4. The interior surfaces of the channels 4 may be imparted with a hydrophilic property so that the liquid specimens can properly be retained in analysis areas of the channels 4.

The liquid specimen analysis disk assembly further includes a guide member 8 detachably provided on the disk 1 for guiding a distal portion 6 of a specimen injector toward each of the specimen injection ports 3 for injection of the liquid specimen. The guide member 8 is composed of a resin or the like, and has guide holes 7.

The guide member 8 includes a tubular body, an annular flange 8a extending from one peripheral edge (upper peripheral edge) of the tubular body and having the guide holes 7 formed as extending therethrough, and a step 8b provided on the other peripheral edge (lower peripheral edge) of the tubular body and engaged with an inner periphery of the center hole 2 of the disk 1. When the guide member 8 is circumferentially positioned in the center hole 2 of the disk 1 with the step 8b of the tubular body being engaged with the inner periphery of the center hole 2, the centers (center axes) of the guide holes 7 are generally aligned with the centers (center axes) of the respective specimen injection ports 3 with the flange 8a being properly spaced from the surface of the disk. The guide holes 7 each have an inner diameter such as to be fitted around the conical distal portion 6 of the specimen injector at a proper position (adjacent to a distal end of the specimen injector).

When the specimen is to be injected into the channel 4 in the disk 1, the distal portion 6 of the specimen injector is inserted into the guide hole 7 of the guide member 8, and a piston (not shown) of the specimen injector is depressed. Thus, the liquid specimen 9 (hereinafter referred to simply as "specimen 9") is injected into the channel 4 through the specimen injection port 3.

At this time, the distal portion 6 of the specimen injector is assuredly guided to the center of the specimen injection port 3 irrespective of the depth of the specimen injection port 3 by inserting the distal portion 6 of the specimen injector into the guide hole 7. Thus, the specimen 9 is prevented from adhering onto the disk surface around the specimen injection port 3.

The insertion depth of the distal portion 6 of the specimen injector is limited with the guide hole 7 being fitted around the distal portion 6, so that the distal end of the specimen injector is positioned intermediate between a lower surface of the guide member 8 (the flange 8a) and the bottom of the specimen injection port 3 (the upper surface of the plate 101). Thus, the distal end of the specimen injector is prevented from contacting the bottom of the specimen injection port 3.

After completion of the injection of the specimens, the guide member 8 is detached from the disk 1, and sealing sheets (not shown) are manually applied onto the disk to seal the respective specimen injection ports 3. The detached guide member 8 is discarded.

Therefore, the specimens 9 never leak out of the disk 1 during the analysis after the injection of the specimens. Even if the distal portion 6 of the specimen injector is displaced from the guide hole 7 during the injection of the specimen and the specimen 9 adheres onto the surface of the guide member 8, there is no possibility that the specimen is scattered around.

As a result, the possibility that an operator touches the specimen can assuredly be eliminated, thereby preventing the infection of the operator.

Figure 3:
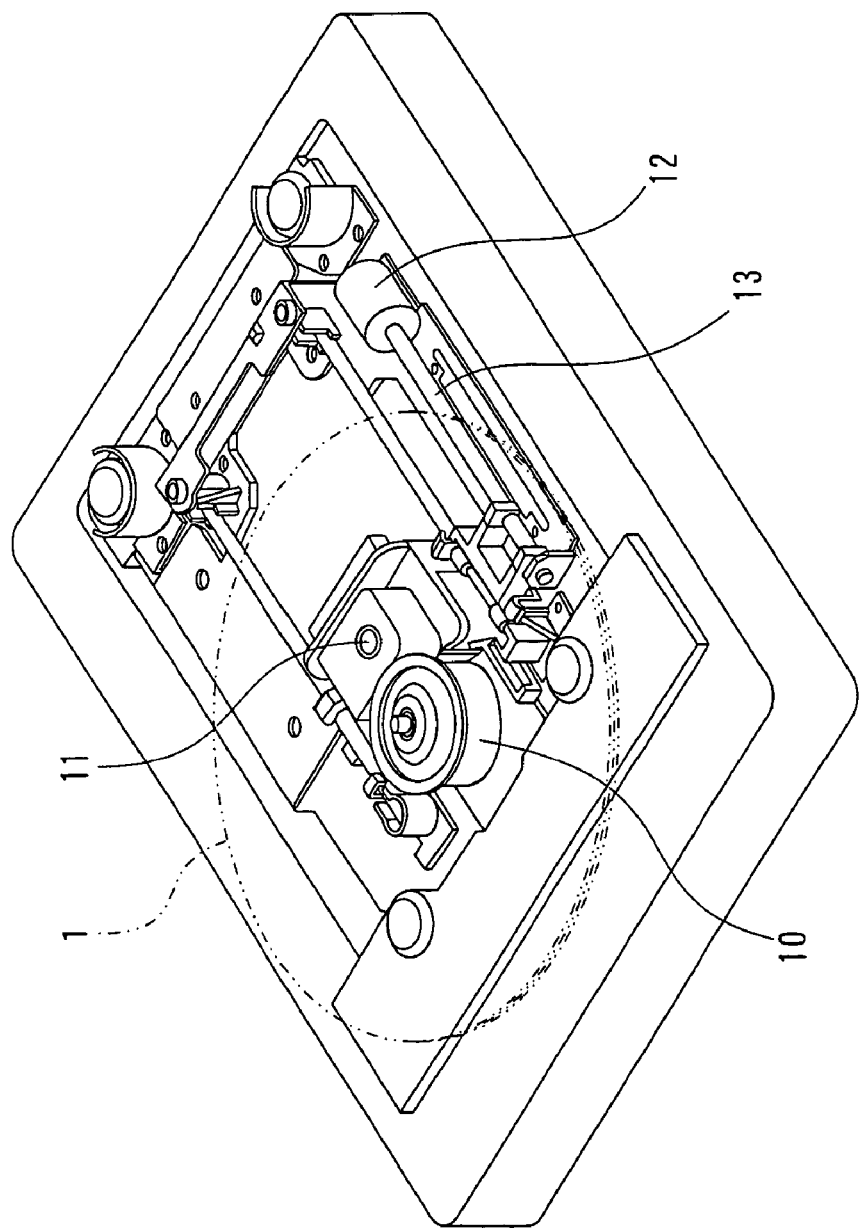
FIG. 3 is a perspective view of a conventional analyzer which performs an analysis with the use of a liquid specimen analysis disk.

FIG. 3 is a perspective view of a liquid specimen analyzer. The analyzer has substantially the same construction as a so-called optical disk device, and includes a spindle motor 10 for rotating the disk 1, an optical pickup 11 for reading information of the specimen by scanning the disk 1, a feed motor 12 for moving the optical pickup 11 radially of the disk 1, a feed screw 13, and the like. The optical disk device is operated according to a predetermined program by a CPU (central processing unit) not shown.

For the analysis, the disk 1 which contains the specimens 9 injected into the channels 4 through the specimen injection ports 3 is set on the spindle motor 10 with the inner periphery thereof being clamped by a damper (not shown), and then rotated by the spindle motor 10. Thus, the specimens 9 are spread in the respective channels 4 by a centrifugal force generated by the rotation. Where the reagent 5 is provided midway of the channels 4, the specimens are allowed to react with the reagent, and the reaction is completed.

While the disk 1 is continuously rotated, a light beam is applied to the specimens 9 or the reagent, and light reflected from the disk or transmitted through the disk is detected by the optical pickup 11. The analysis is performed on the basis of detection signals through image processing by an analyzing section (not shown) provided in the liquid specimen analyzer. That is, information on the specimens 9 and/or the reagent is optically read in synchronization with the rotation for the qualitative/quantitative analysis.

While the disk 1 having a three tier structure has been described in Embodiment 1, the laminate structure of the disk 1 and the numbers and orientations of the specimen injection ports 3 and the channels 4 are not limited to those described above.

(Embodiment 2)

Figure 4:
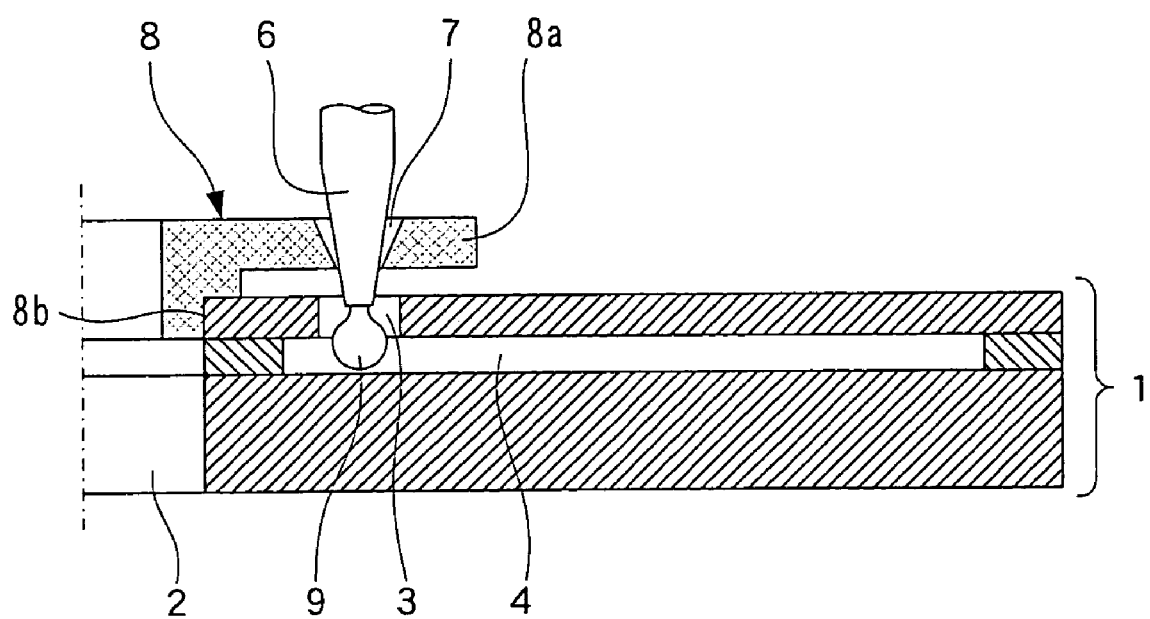
FIG. 4 is an enlarged vertical sectional view illustrating a part of a liquid specimen analysis disk assembly according to Embodiment 2 of the present invention.

FIG. 4 is an enlarged vertical sectional view illustrating a part of a liquid specimen analysis disk assembly according to Embodiment 2 of the present invention. This liquid specimen analysis disk assembly is related to claims 2, 3 and 4.

The liquid specimen analysis disk assembly according to Embodiment 2 has substantially the same construction as the disk assembly according to Embodiment 1, but is different in the shape of each of the guide holes 7 of the guide member 8.

The guide holes 7 of the guide member 8 are each tapered so that a lower end opening thereof opposed to the specimen injection port 3 has a smaller diameter than an upper end opening thereof facing away from the specimen injection port 3. Further, the lower end opening of the guide hole 7 has an inner diameter slightly greater than the outer diameter of the distal end of the conical distal portion 6 of the specimen injector, and has a smaller inner diameter than the specimen injection port 3.

Therefore, when the distal portion 6 of the specimen injector is inserted into the guide hole 7, the distal portion 6 can easily and assuredly be guided to the center of the specimen injection port 3, because the guide hole 7 of the guide member 8 and the distal portion 6 of the specimen injector have a tapered interior surface and a conical exterior surface, respectively, and the lower end opening of the guide hole 7 has a smaller inner diameter than the specimen injection port 3.

At this time, the distal end of the specimen injector is positioned intermediate between the lower surface of the guide member 8 (flange 8a) and the bottom of the specimen injection port 3 (the upper surface of the plate 101) with the guide hole 7 being fitted around the distal portion 6 of the specimen injector. Thus, the distal end of the specimen injector is prevented from contacting the bottom of the specimen injection port 3.

Therefore, the specimen 9 ejected from the distal end of the specimen injector is prevented from adhering onto the periphery of the guide hole 7 of the guide member 8, onto the disk surface around the specimen injection port 3 and onto the exterior surface of the distal portion 6 of the specimen injector.

Thus, the possibility that the operator touches the specimen 9 thereby to be infected with a pathogen can be further reduced as compared with the liquid specimen analysis disk assembly according to Embodiment 1.

(Embodiment 3)

Figure 5:
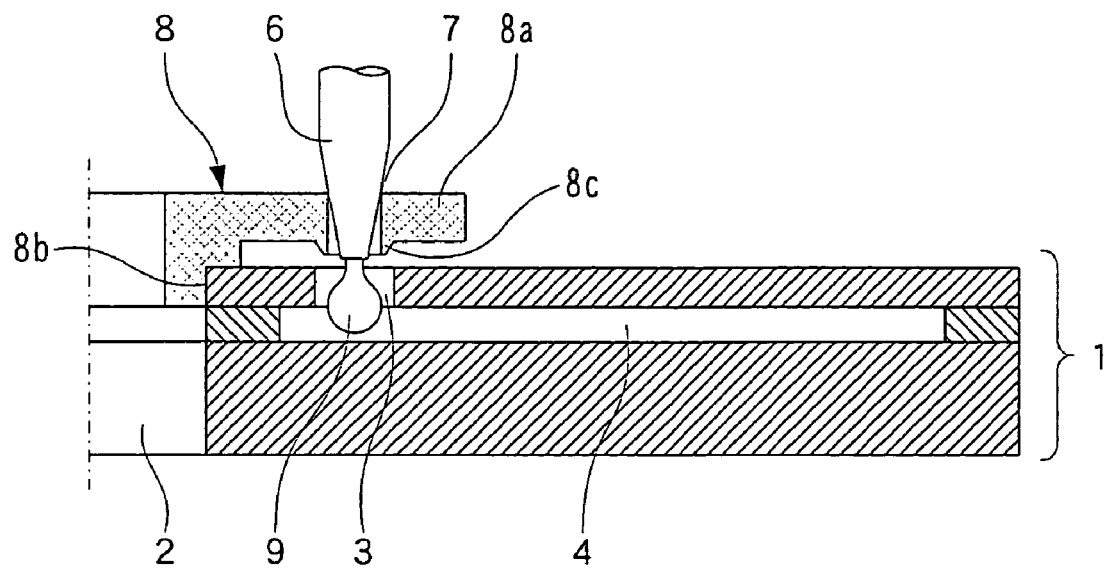
FIG. 5 is an enlarged vertical sectional view illustrating a part of a liquid specimen analysis disk assembly according to Embodiment 3 of the present invention.

FIG. 5 is an enlarged vertical sectional view illustrating a part of a liquid specimen analysis disk assembly according to Embodiment 3 of the present invention. This liquid specimen analysis disk assembly is related to claims 5 and 6.

The liquid specimen analysis disk assembly according to Embodiment 3 has substantially the same construction as the disk assembly according to Embodiment 1, but differs in that the guide member 8 has tubular projections 8c provided on the lower surface of the flange 8a thereof as surrounding the respective guide holes 7. The tubular projections 8c each have a distal end having an outer diameter smaller than the inner diameter of the specimen injection port 3.

Therefore, even if the specimen 9 ejected from the distal portion 6 of the specimen injector adheres onto the interior surface of the guide hole 7, the specimen does not spread outward beyond the tubular projection 8c, so that the specimen adhesion area can be minimized. Even if the specimen 9 adhering onto the interior surface of the guide hole 7 drips, the specimen drips into the specimen injection port 3 from the distal end of the tubular projection 8c having an outer diameter smaller than the inner diameter of the specimen injection port 3. This prevents the specimen from adhering onto the disk surface.

Thus, the possibility that the operator touches the specimen 9 thereby to be infected with a pathogen can be further reduced as compared with the liquid specimen analysis disk assembly according to Embodiment 1.

(Embodiment 4)

Figure 6:
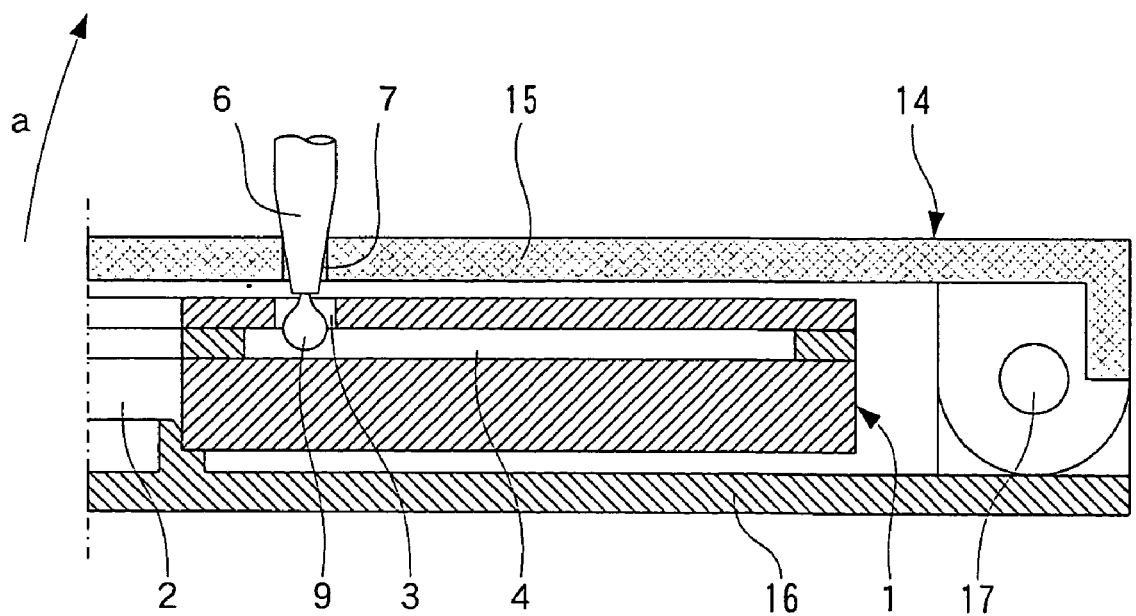
FIG. 6 is an enlarged vertical sectional view illustrating a part of a liquid specimen analysis disk assembly according to Embodiment 4 of the present invention.

FIG. 6 is an enlarged vertical sectional view illustrating a part of a liquid specimen analysis disk assembly according to Embodiment 4 of the present invention. This liquid specimen analysis disk assembly is related to claims 5 and 6.

The liquid specimen analysis disk assembly according to Embodiment 4 has substantially the same construction as the disk assembly according to Embodiment 1, but differs in that the guide member 8 described in Embodiment 1 is constituted by a lid 15 of a disk case 14.

The disk case 14 is a thin resin box which is capable of containing the disk 1. The disk case 14 includes a case body 16 in which the disk 1 is retained with its center hole 2 properly positioned, and a planar lid 15 hinged to one side of the case body 16 via a hinge 17. The lid 15 is pivotal about the pivot axis of the hinge 17 so as to be opened and closed. The lid 15 is formed with the guide holes 7 in association with the respective specimen injection ports 3.

When the specimen is to be injected, the disk 1 is retained in the case body 16 with the lid 15 being closed, and the distal portion 6 of the specimen injector is guided to the center of the specimen injection port 3 of the disk 1 through the guide hole 7. Then, the specimen 9 is injected into the channel 4 through the specimen injection port 3. After completion of the injection of the specimen, the lid 15 is pivoted in a direction a to be opened, and the specimen injection port 3 of the disk 1 is sealed. Then, the disk 1 is taken out of the case body 16.

Thus, the possibility that the operator touches the specimen 9 thereby to be infected with a pathogen can be further reduced as compared with the liquid specimen analysis disk assembly according to Embodiment 1.

Since the guide member is constituted by the lid 15 of the conventionally used disk case 14, the number of the components can be reduced. The lid 15 (guide member) can be separated from the disk 1 when the disk is taken out of the disk case. Hence, there is no need to separately perform a guide member detaching operation, thereby simplifying the operation procedure as compared with the liquid specimen analysis disk assembly according to Embodiment 1.

(Embodiment 5)

Figure 7A:
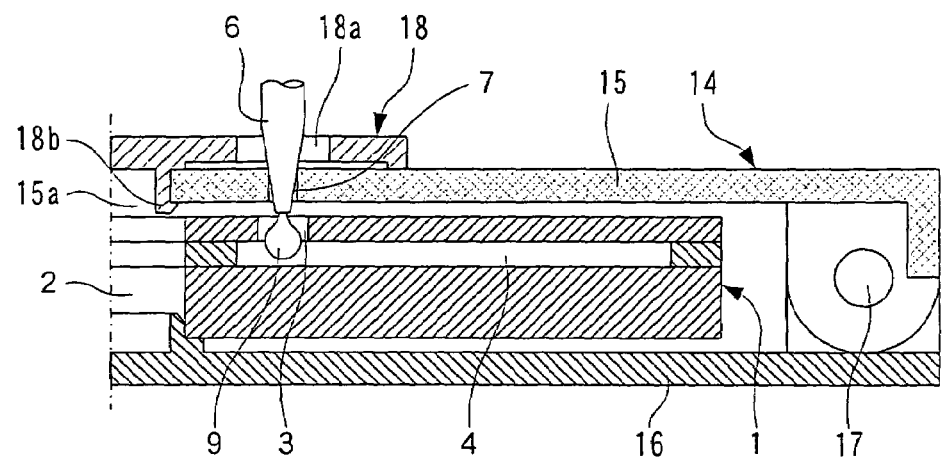
FIGS. 7A and 7B are enlarged vertical sectional views each illustrating a part of a liquid specimen analysis disk assembly according to Embodiment 5 of the present invention.
Figure 7B:
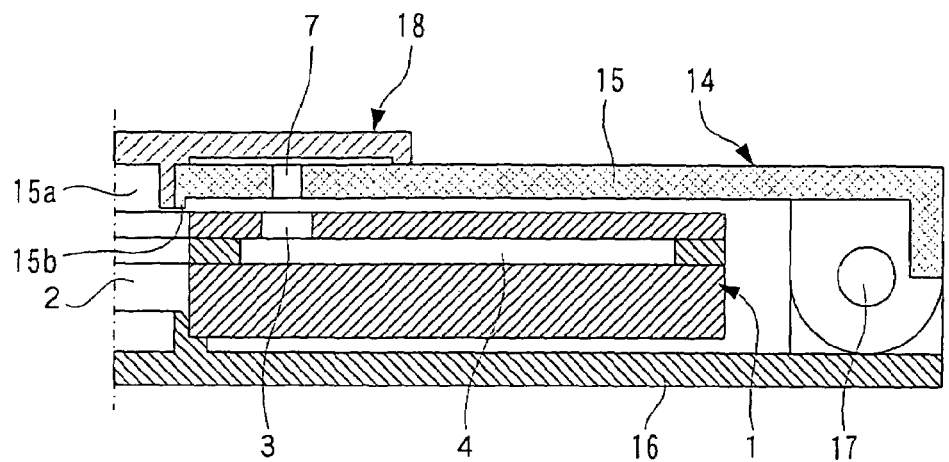

FIGS. 7A and 7B are enlarged vertical sectional views each illustrating a part of a liquid specimen analysis disk assembly according to Embodiment 5 of the present invention. This liquid specimen analysis disk assembly is related to claims 8, 9 and 10.

The liquid specimen analysis disk assembly according to Embodiment 5 has substantially the same construction as the disk assembly according to Embodiment 4, but differs in that a cover member 18 for opening and closing the guide holes 7 is provided on the lid 15.

The cover member 18 is composed of a resin, and has a disk shape. The cover member 18 has a tubular portion which is fitted in a center hole 15a formed in the lid 15 rotatably about its axis. The cover member 18 has an opening 18a having a size such as not to prevent the insertion of the distal portion 6 of the specimen injector in the guide hole 7.

A surface of the cover member 18 opposed to the disk case 14 is spaced from an upper surface of the lid 15 of the disk case 14 with only a peripheral portion thereof being in intimate contact with the upper surface of the lid 15. The center tubular portion of the cover member 18 has an engagement claw 18b provided at a predetermined position on an outer periphery thereof, and the lid 15 also has an engagement claw 15b provided at a predetermined position on an inner periphery thereof defining the center hole 15a. The claw 18b is engaged with the claw 15b on the circumference of the center hole 15a. The claw 18b is also engaged with the rear surface of the lid 15 so as to permit the rotation of the cover member 18. The claw 15b functions as a stopper for stopping the rotation of the cover member 18 in abutment against the claw 18b.

When the specimen is to be injected, the distal portion 6 of the specimen injector is inserted into the opening 18a of the cover member 18 and the guide hole 7 and guided to the center of the specimen injection port 3 through the guide hole 7 with the opening 18a being opposed with the guide hole 7 as shown in FIG. 7A. Then, the specimen 9 is injected into the channel 4 through the specimen injection port 3. After completion of the injection of the specimen, the cover member 18 is rotated about the axis thereof to cover the guide hole 7 with a solid portion of the cover member 18 as shown in FIG. 7B.

At this time, the cover member 18 is rotated parallel to the disk surface, so that a space for the opening and closing of the guide holes 7 is not particularly required. Further, when the cover member 18 is rotated to a position at which the guide holes 7 are closed as shown in FIG. 7B, the claw 18b is engaged with the claw 15b to prevent the cover member 18 from being rotated in a reverse direction.

Therefore, even if the specimen 9 ejected from the distal portion 6 of the specimen injector adheres onto the periphery of the guide hole 7 of the guide member 8, the periphery of the guide hole 7 is covered with the cover member 18 after the injection of the specimen. Further, the operator is prevented from inadvertently opening the cover member 18 and, hence, prevented from touching the specimen 9.

The shape of the cover member 18 is not limited to the disk shape, but may be configured in various ways. For example, the cover member 18 may be configured such as to extend radially from the tubular portion.

(Embodiment 6)

Figure 8A:
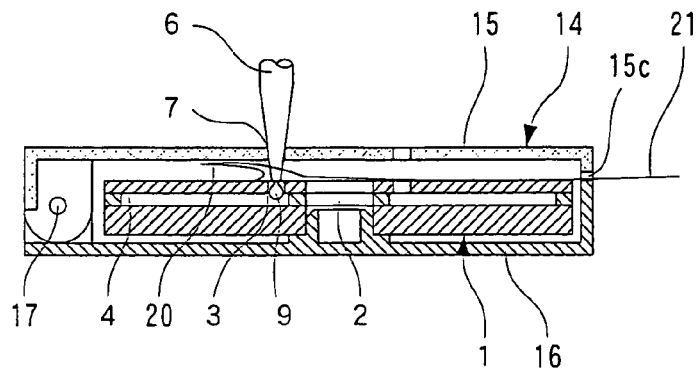
FIGS. 8A to 8C are vertical sectional views of a liquid specimen analysis disk assembly according to Embodiment 6 of the present invention.
Figure 8B:
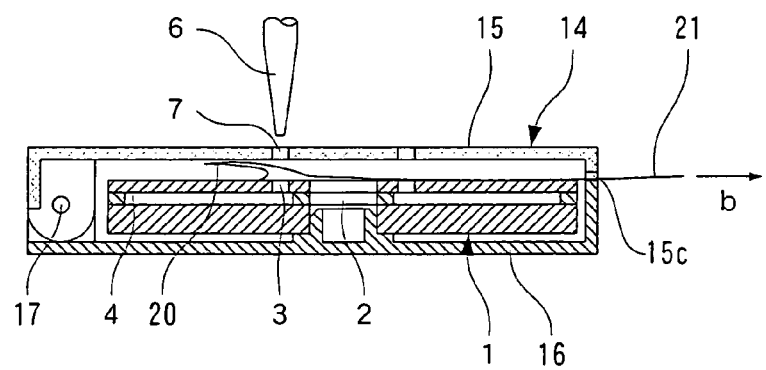
Figure 8C:
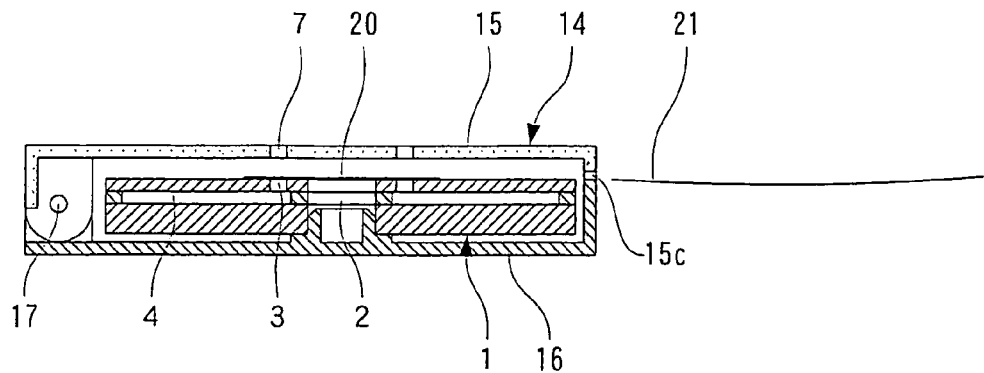

FIGS. 8A to 8C are vertical sectional views of a liquid specimen analysis disk assembly according to Embodiment 6 of the present invention. This liquid specimen analysis disk assembly is related to claim 11.

The liquid specimen analysis disk assembly according to Embodiment 6 has substantially the same construction as the disk assembly according to Embodiment 4, but differs in that a sealing sheet 20 for sealing the specimen injection ports 3 is retained in a folded state (or in a rolled state) between the lid 15 and the disk 1.

The sealing sheet 20 includes a water-proof paper or polyethylene sheet on which an adhesive is applied, and has a round shape such as to cover a center portion of the disk formed with the plural specimen injection ports 3. A portion of the sealing sheet 20 adjacent to the hinge 17 on a center line extending through the center of the disk 1 is fixed to the disk 1, and a string tab 21 is attached to a portion of the sealing sheet 20 opposite from the fixed portion. The tab 21 is composed of a flexible paper or polyethylene sheet having a predetermined strength. An end portion of the tab 21 extends to the outside through an opening 15c formed in a side portion of the lid 15 opposite from the hinge 17.

When the specimen is to be injected, the distal portion 6 of the specimen injector is guided to the center of the specimen injection port 3 through the guide hole 7 with the sealing sheet 20 being retained in the folded state (or in the rolled state) as shown in FIG. 8A. Then, the specimen 9 is injected into the channel 4 through the specimen injection port 3. The string tab 21 is located in a position where the insertion of the distal portion 6 of the specimen injector in the specimen injection port 3 is not hindered.

After completion of the injection of the specimen, the tab 21 is pulled in an arrow direction b as shown in FIG. 8B to extend the sealing sheet 20, which is in turn applied to the center portion of the disk to seal the specimen injection ports 3. The tab 21 is further pulled to be separated from the sealing sheet 20 and extracted to the outside through the opening 15c as shown in FIG. 8C. Thereafter, the lid 15 is opened, and the disk 1 is taken out.

Therefore, the operator can safely handle the disk 1 without touching the specimen.

(Embodiment 7)

Figure 9A:
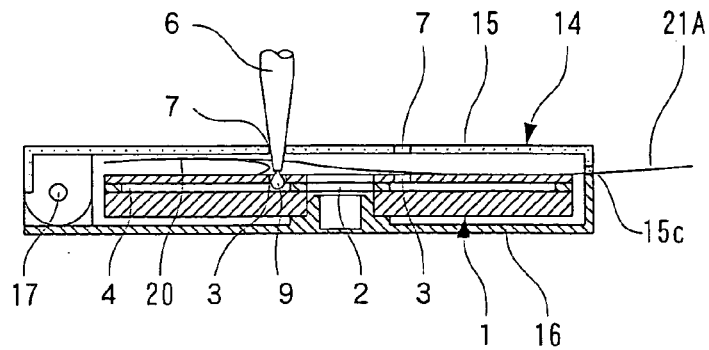
FIGS. 9A to 9C are vertical sectional views of a liquid specimen analysis disk assembly according to Embodiment 7 of the present invention.
Figure 9B:
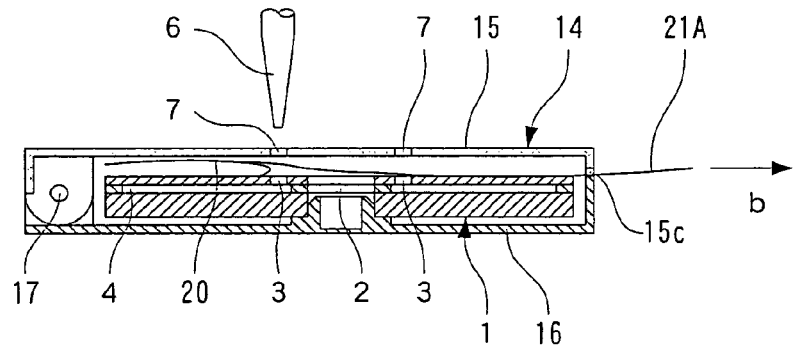
Figure 9C:
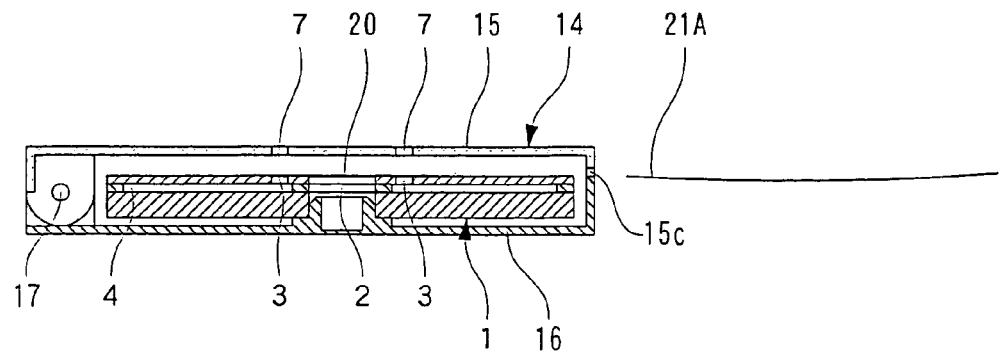

FIGS. 9A to 9C are vertical sectional views of a liquid specimen analysis disk assembly according to Embodiment 7 of the present invention. This liquid specimen analysis disk assembly is related to claim 12.

The liquid specimen analysis disk assembly according to Embodiment 7 has substantially the same construction as the disk assembly according to Embodiment 6, but differs in that the sealing sheet 20 retained between the lid 15 and the disk 1 for sealing the specimen injection ports 3 is adapted to entirely cover the disk 1 and a tab 21A is constituted by a part of a releasable sheet which lines the sealing sheet 20.

As in the case of the liquid specimen analysis disk assembly according to Embodiment 6, the specimen 9 is injected into the channel 4 through the specimen injection port 3 with the sealing sheet 20 being retained in the folded state as shown in FIG. 9A. After completion of the injection of the specimen, the tab 21A is pulled, whereby the sealing sheet 20 is extended to seal the specimen injection ports 3 as shown in FIG. 9B. Then, the tab 21A is extracted to the outside through the opening 15c as shown in FIG. 9C.

At this time, the releasable sheet can smoothly be removed from the sealing sheet 20 to extend the sealing sheet 20, because the tab 21A is constituted by a part of the releasable sheet.

Therefore, the handling ease is improved as compared with the liquid specimen analysis disk assembly according to Embodiment 6 in which the sealing sheet 20 is folded with its adhesive surface portions adhering to each other (see FIG. 8A).

(Embodiment 8)

Figure 10A:
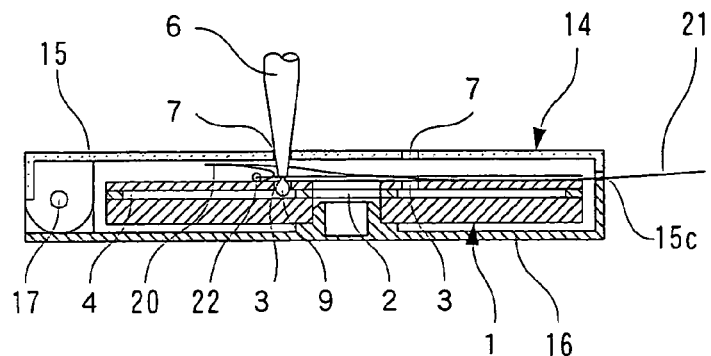
FIGS. 10A to 10D are vertical sectional views of a liquid specimen analysis disk assembly according to Embodiment 8 of the present invention.
Figure 10B:
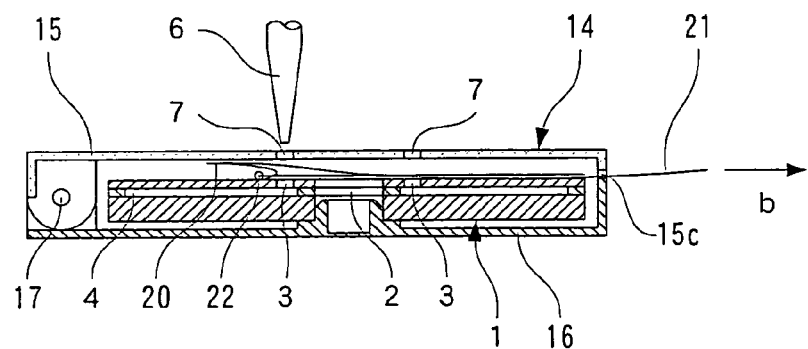
Figure 10C:
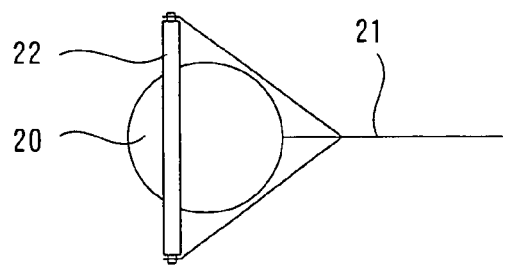
Figure 10D:
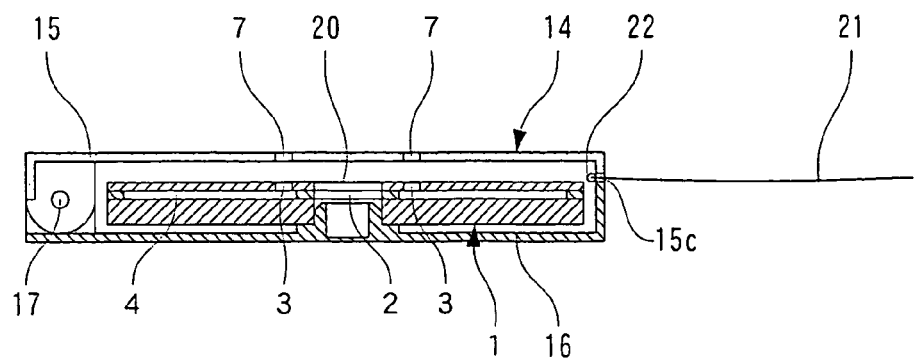

FIGS. 10A, 10B and 10D are vertical sectional views of a liquid specimen analysis disk assembly according to Embodiment 8 of the present invention. FIG. 10C is a plan view for explaining how to extend a sealing sheet. This liquid specimen analysis disk assembly is related to claim 13.

In the liquid specimen analysis disk assembly according to Embodiment 8, the sealing sheet 20 for sealing the specimen injection ports 3 is retained in a folded state (or in a rolled state) between the lid 15 and the disk surface as in the disk assembly according to Embodiment 6. However, a thin cylindrical roller member 22 such as of a rubber for pressing the extended sealing sheet 20 against the disk surface is connected to the tab 21. One end of the tab 21 is connected to the periphery of the round sealing sheet 20 and, when a force of greater than a predetermined magnitude is applied to the tab 21, the tab 21 is separated from the sealing sheet 20. Further, the tab 21 is connected to opposite ends of the roller member 22.

As in the case of the liquid specimen analysis disk assembly according to Embodiment 6, the specimen 9 is injected into the channel 4 through the specimen injection port 3 with the sealing sheet 20 being retained in the folded state (or in the roller state) as shown in FIG. 10A. After completion of the injection of the specimen, the tab 21 is pulled, whereby the sealing sheet 20 is extended as shown in FIG. 10B. At the same time, the roller member 20 moves over the sealing sheet 20, whereby the specimen injection ports 3 are sealed. Then, the tab 21 is separated from the sealing sheet 20, and the roller member 20 is pulled toward the opening 15c as shown in FIG. 10D.

At this time, as shown in FIG. 10C, the roller member 22 is rolled to press the extended sealing sheet 20 against the disk surface, as the tab 21 is pulled.

Therefore, the handling ease is improved as compared with the liquid specimen analysis disk assembly according to Embodiment 6, because the sealing sheet 20 is assuredly automatically applied onto the disk surface.

(Embodiment 9)

Figure 11A:
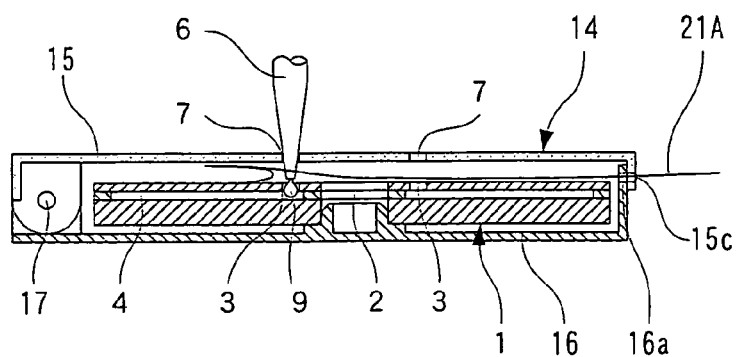
FIGS. 11A to 11C are vertical sectional views of a liquid specimen analysis disk assembly according to Embodiment 9 of the present invention.
Figure 11B:
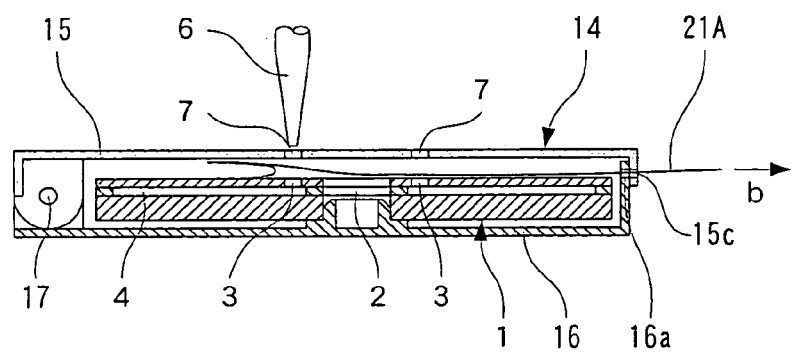
Figure 11C:
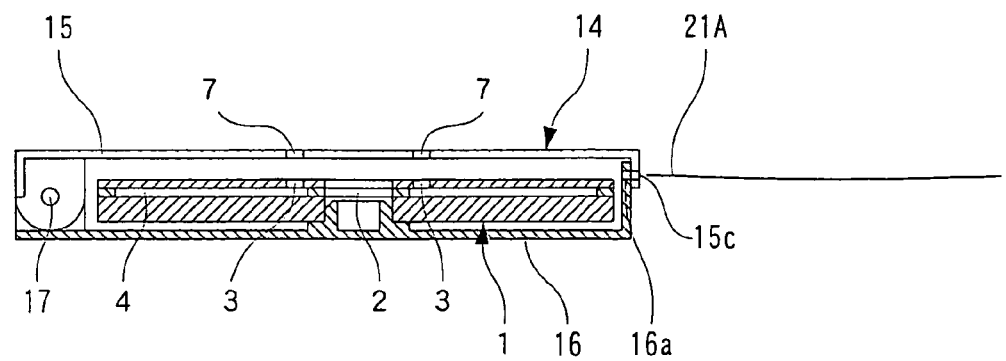

FIGS. 11A to 11C are vertical sectional views of a liquid specimen analysis disk assembly according to Embodiment 9 of the present invention. This liquid specimen analysis disk assembly is related to claim 14.

In the liquid specimen analysis disk assembly according to Embodiment 9, the sealing sheet 20 for sealing the specimen injection ports 3 is retained in a folded state (or in a rolled state) between the lid 15 and the disk surface as in the disk assembly according to Embodiment 6. However, at least a portion of the outer periphery of the lid 15 opposite from the hinge 17 is folded to overlap with the outer peripheral wall of the case body 16, and the tab 21A extends outward through openings 15c, 16a respectively formed in overlapped portions of the lid 15 and the case body 16.

As in the case of the liquid specimen analysis disk assembly according to Embodiment 6, the specimen 9 is injected into the channel 4 through the specimen injection port 3 with the sealing sheet 20 being retained in the folded state (or in the rolled state) as shown in FIG. 11A. After completion of the injection of the specimen, the tab 21A is pulled, whereby the sealing sheet 20 is extended to seal the specimen injection ports 3 as shown in FIG. 11B. Then, the tab 21A is extracted to the outside through the openings 15c, 16a as shown in FIG. 11C.

With this liquid specimen analysis disk assembly, however, the tab 21A hinders the lid 15 from being opened, unless the tab 21A is extracted through the openings 15c, 16a. In other words, the lid 15 is permitted to be opened only after completion of the sealing of the specimen injection ports 3. With the sealing uncompleted, the operator is prevented from inadvertently opening the lid 15.

Therefore, the operator is assuredly prevented from touching the specimen 9 as compared with the liquid specimen analysis disk assembly according to Embodiment 6.

(Embodiment 10)

Figure 12:
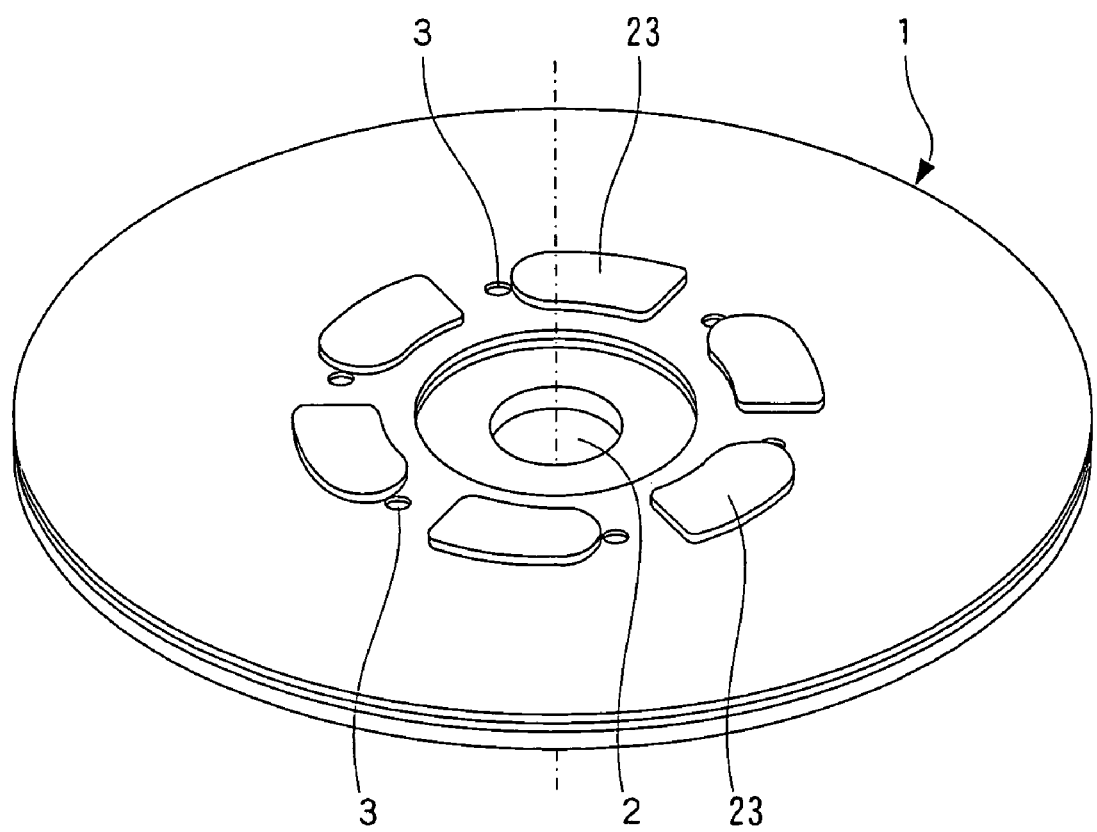
FIG. 12 is a perspective view of a liquid specimen analysis disk assembly according to Embodiment 10 of the present invention.
Figure 13A:
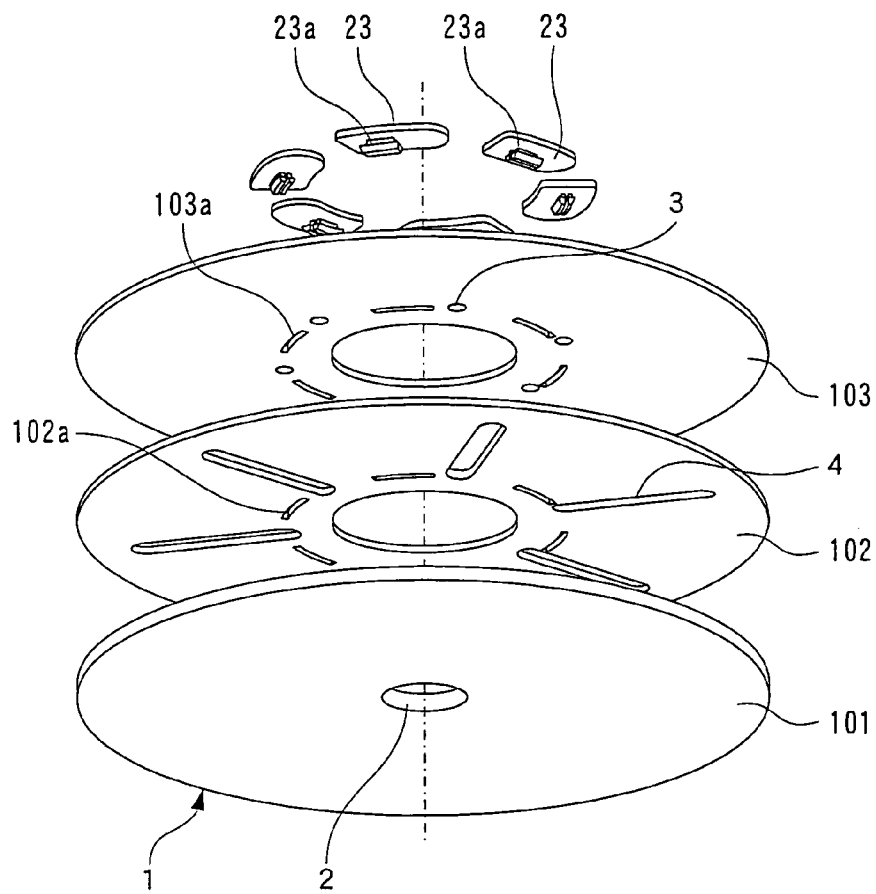
FIG. 13A is an exploded perspective view of the liquid specimen analysis disk assembly of FIG. 12.
Figure 13B:
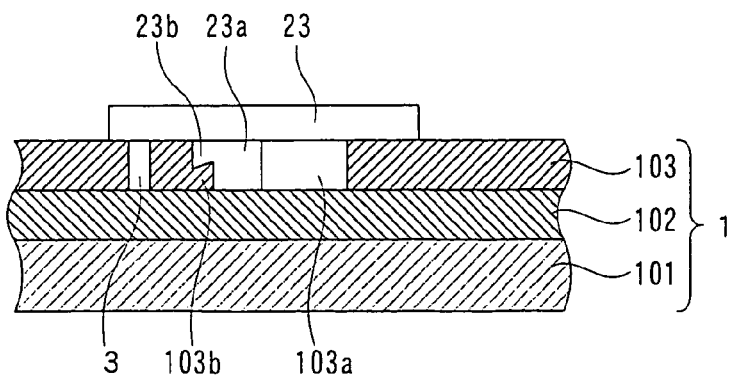
FIG. 13B is a partial sectional view of the liquid specimen analysis disk assembly according to Embodiment 10 of the present invention.

FIG. 12 is a perspective view of a liquid specimen analysis disk assembly according to Embodiment 10 of the present invention. FIG. 13 is an exploded perspective view of the liquid specimen analysis disk assembly of FIG. 12. This liquid specimen analysis disk assembly is related to claims 15 and 16.

The liquid specimen analysis disk assembly according to Embodiment 10 includes a disk 1 having substantially the same construction as the disk 1 employed in Embodiment 1, and further includes a plurality of seal members 23 provided on the upper surface of the third plate 103 for sealing the respective specimen injection ports 3.

The second plate 102 of the disk 1 has slits 102a formed in an inner peripheral portion thereof between the radially innermost ends of the respective channels 4 alongside an inner periphery thereof. Further, the third plate 103 has slits 103a formed in an inner peripheral portion thereof between the specimen injection ports 3 alongside an inner periphery thereof. The seal members 23 are composed of a resin such as polyacetal which provides an excellent slidability. The seal members 23 each have a generally planar shape, and are curved along the inner periphery of the disk 1. The seal members 23 each have a projection 23a provided on a lower surface thereof in engagement with the slits 102a, 103a of the disk 1, and are each slidable between a position at which the specimen injection port 3 is opened and a position at which the specimen injection port 3 is closed.

The seal members 23 each have a claw 23b, and the slits 103a each have a claw 103b. The claws 23b and 103b are brought into engagement with each other when the seal member 23 is slid to the position at which the specimen injection port 3 is closed (FIG. 13B), thereby preventing the seal member 23 from sliding in a reverse direction.

After completion of the injection of the specimen, the specimen injection ports 3 can individually speedily be sealed simply by sliding the seal members 23. With the specimen injection ports 3 being sealed, the claws 23b are respectively engaged with the claws 103b, thereby preventing the operator from inadvertently sliding the seal members 23 to open the specimen injection ports 3.

This assuredly prevents the operator from touching the specimen 9 adhering onto the peripheries of the specimen injection ports 3, and assuredly prevents the specimen 9 from leaking out of the specimen injection ports 3.

The shapes of the seal members 23 and the slits 102a, 103a and the sliding direction are not limited to those described above, but may be changed as desired.

(Embodiment 11)

Figure 14A:
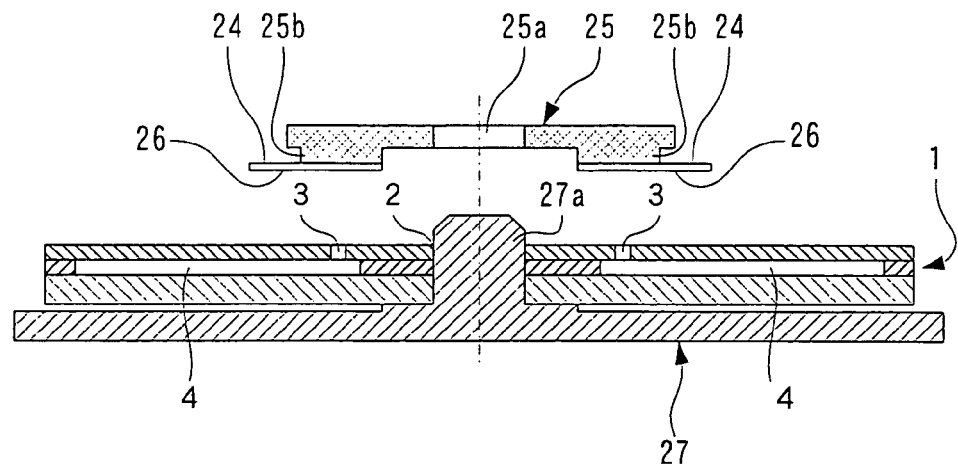
FIG. 14A is a sectional view of a liquid specimen analysis disk assembly according to Embodiment 11 of the present invention.
Figure 14B:
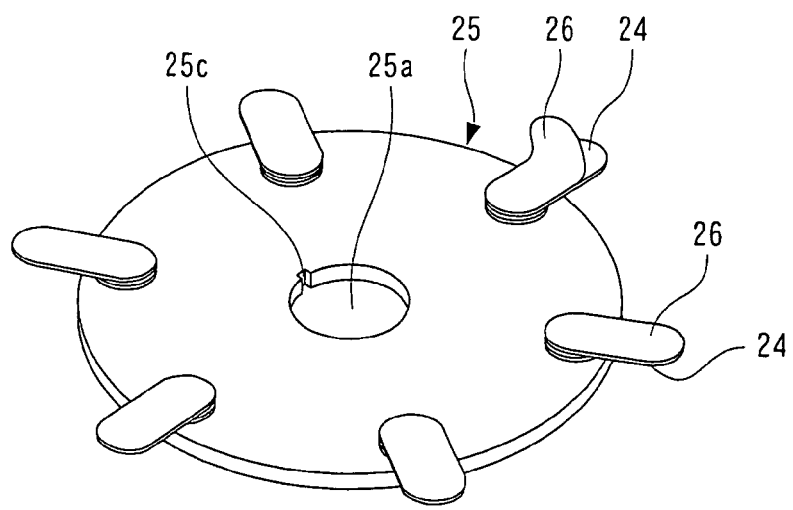
FIG. 14B is a perspective view of a temporary seal retaining member of the liquid specimen analysis disk assembly according to Embodiment 11 of the present invention.

FIG. 14A is a sectional view of a liquid specimen analysis disk assembly according to Embodiment 11 of the present invention, and FIG. 14B is a perspective view of a temporary seal retaining member of the liquid specimen analysis disk assembly. This liquid specimen analysis disk assembly is related to claims 17 and 18.

The liquid specimen analysis disk assembly according to Embodiment 11 includes a disk 1 having the same construction as the disk 1 employed in Embodiment 1, and further includes a temporary seal retaining member 25 which is detachable from the disk 1 and temporarily retains a plurality of adhesive sealing sheets 24 for sealing the respective specimen injection ports 3.

The temporary seal retaining member 25 is composed of a resin or the like, and has a generally disk shape. The temporary seal retaining member 25 has a center hole 25a having the same diameter as the disk 1, and protuberances 25b provided in association with the specimen injection ports 3 of the disk 1 and each having a flat surface parallel to the disk surface. The adhesive sealing sheets 24 are temporarily retained on the flat surfaces of the respective protuberances 25b with the adhesive surfaces thereof facing away from the flat surfaces. The sealing sheets 24 each include a water-proof paper or polyethylene sheet on which an adhesive is applied, and a releasable sheet 26 which covers the adhesive surface of the water-proof sheet.

The protuberances 25b of the temporary seal retaining member 25 (or the entire temporary seal retaining member 25) are each composed of a resilient material such as a sponge or a rubber. The temporary seal retaining member 25 has a positioning notch 25c formed in an inner periphery of the temporary seal retaining member 25 around the center hole 25a.

The disk 1 having the aforesaid construction is fitted around a center projection 27a of a disk base 27 as shown in FIG. 14A, and then the specimen is injected through any of the specimen injection ports 3 into the disk 1.

After completion of the injection of the specimen, the temporary seal retaining member 25 is positioned with respect to the disk surface by the notch 25c, and engaged with the center projection 27a of the disk base 27. Then, the releasable sheet 26 is removed from the sealing sheet 24 associated with the specimen injection port 3 used for the injection of the specimen, and the temporary seal retaining member 25 is pressed against the disk 1. Thus, the sealing sheet 24 is applied only onto the used specimen injection port 3 (onto the disk surface around the specimen injection port 3) to seal the specimen injection port 3.

Since the protuberances 25b of the temporary seal retaining member 25 are composed of the resilient material, the sealing sheet 24 can be pressed with a uniform pressure for the application thereof. Thus, the specimen injection port 3 can assuredly be sealed.

Therefore, even if the specimens adhere onto the peripheries of the specimen injection ports 3, the operator can assuredly and speedily seal the specimen injection ports 3 individually without touching the specimens.

(Embodiment 12)

Figure 15:
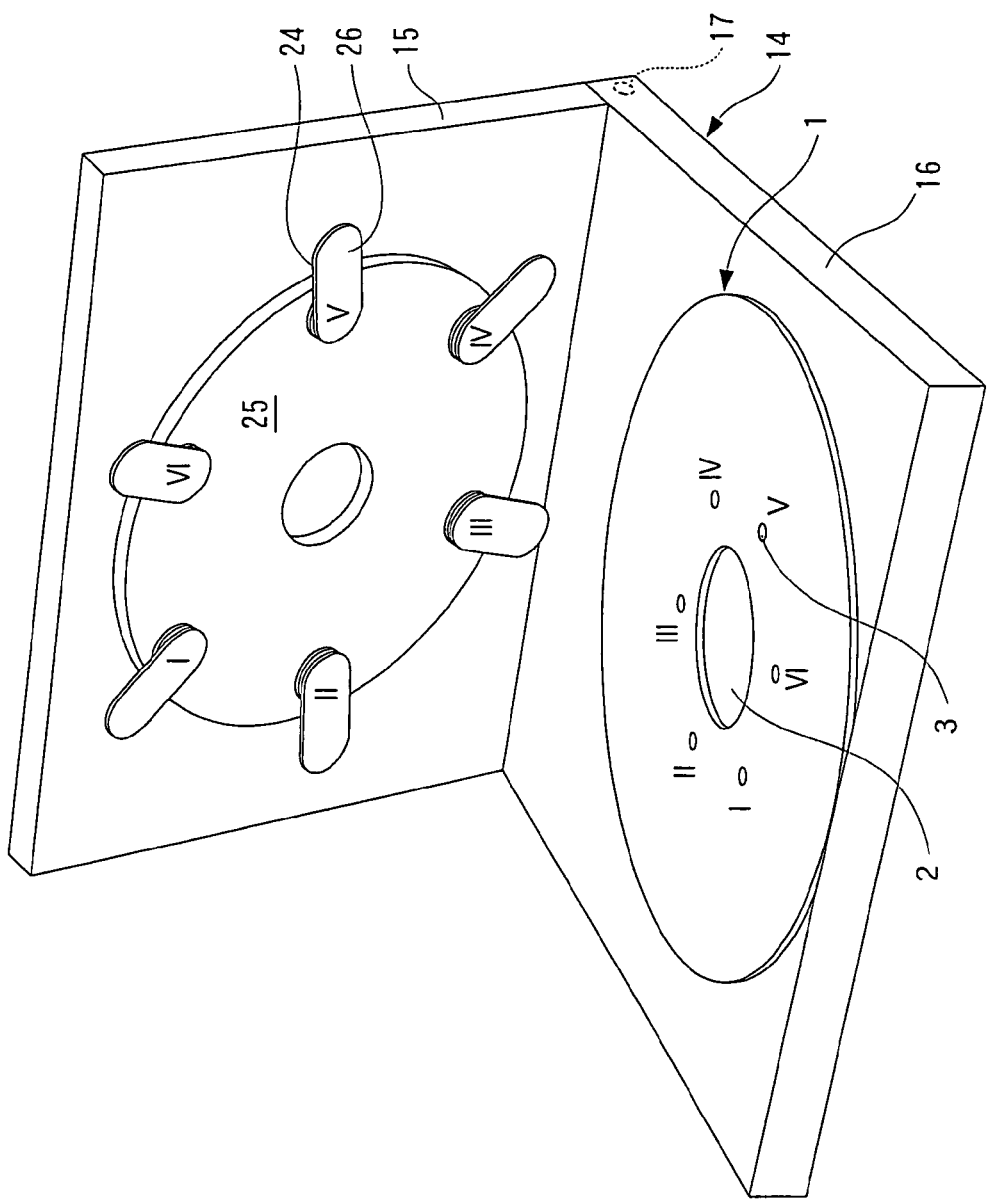
FIG. 15 is a perspective view of a liquid specimen analysis disk assembly according to Embodiment 12 of the present invention.

FIG. 15 is a perspective view of a liquid specimen analysis disk assembly according to Embodiment 12 of the present invention. This liquid specimen analysis disk assembly is related to claims 19 to 21.

The liquid specimen analysis disk assembly according to Embodiment 12 has substantially the same construction as the disk assembly according to Embodiment 11, but differs in that the temporary seal retaining member 25 is provided integrally with the lid 15 which is pivotal about a pivot axis of a hinge 17 provided in a disk case 14.

First identification marks having different characters (numerals in this embodiment) are provided in the vicinity of the respective specimen injection ports 3 of the disk 1, and second identification marks having characters (numerals) corresponding to the characters of the first identification marks are provided on the releasable sheets 26 of the sealing sheets 24 (or on the sealing sheets 24 per se or on portions of the temporary seal retaining member 25 adjacent to the sealing sheets 24) associated with the respective specimen injection ports 3.

With the lid 15 of the disk case 14 being opened, the specimen is injected through any of the specimen injection ports 3 into the disk 1 in the case 14.

After completion of the injection of the specimen, the releasable sheet 26 corresponding to the specimen injection port 3 used for the injection of the specimen is removed with reference to the first and second identification marks, and then the lid 15 is pivoted about the pivot axis of the hinge 17 so as to be closed. Thus, the sealing sheet 24 can be applied only onto the used specimen injection port 3 (on the disk surface around the specimen injection port 3).

At this time, the specimen injection port 3 can be sealed simply by closing the lid 15 without positioning, because the temporary seal retaining member 25 is provided integrally with the lid 15 to realize a simplified sealing mechanism. The correspondences between the specimen injection ports 3 and the sealing sheets 24 can easily visually identified by the first and second identification marks. This prevents erroneous removal of the releasable sheet 26.

Therefore, even if the specimens adhere onto the peripheries of the specimen injection ports, the operator can speedily individually seal the specimen injection ports 3 without touching the specimens.

The temporary seal retaining member 25 may be provided separately from the lid 15 (for example, provided in the form of an inner lid), and adapted to pivot about the pivot axis of the hinge 17 provided in the disk case 14.

(Embodiment 13)

Figure 16:
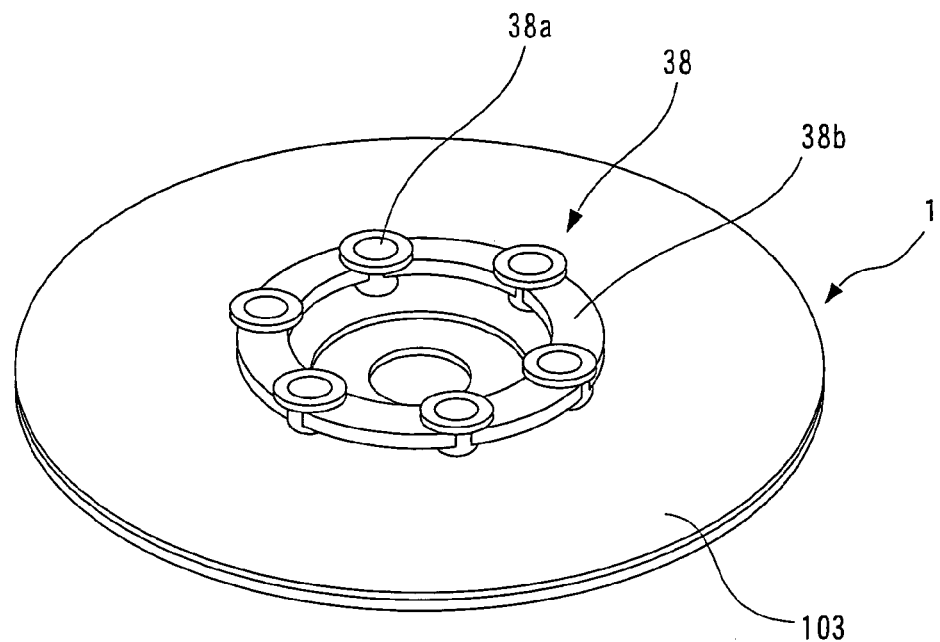
FIG. 16 is a perspective view of a liquid specimen analysis disk assembly according to Embodiment 13 of the present invention.
Figure 17:
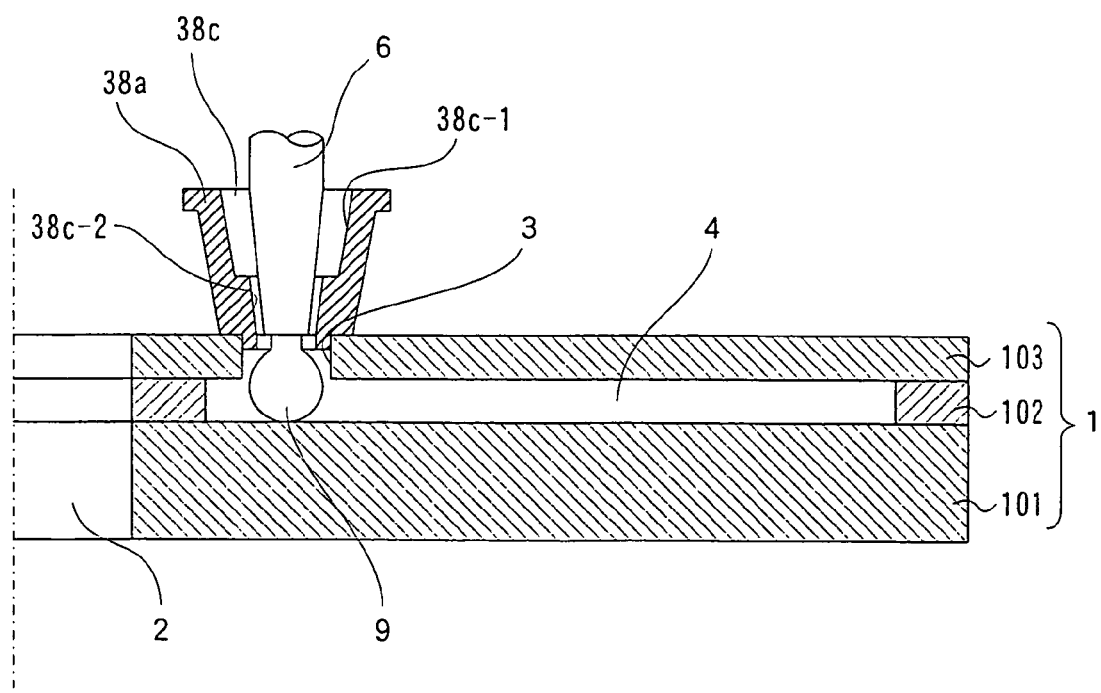
FIG. 17 is a partial sectional view of the liquid specimen analysis disk assembly according to Embodiment 13 of the present invention.

FIG. 16 is a perspective view of a liquid specimen analysis disk assembly according to Embodiment 13 of the present invention, and FIG. 17 is a partial sectional view of the liquid specimen analysis disk assembly. This liquid specimen analysis disk assembly is related to claims 22 and 23.

The disk assembly according to Embodiment 13 includes a disk 1 having the same construction as the disk 1 employed in Embodiment 1, and further includes a guide member 38 detachably provided over the specimen injection ports 3. The guide member 38 includes six introduction portions 38a provided in association with the six specimen injection ports 3, and a ring plate 38b connecting the introduction portions 38a to one another.

The introduction potions 38a each has a truncated cone shape and formed in the center thereof with a guide hole 38c having a upper and lower two-stage structure in order for guiding thereinto the distal portion 6 of the specimen injector. The upper guide hole portion 38c-1 has an inner diameter greater than the outer diameter of the distal portion 6 of the specimen injector. The upper guide hole portion 38c-1 is tapered as having a diameter progressively decreasing toward its lower end, and connected to the lower guide hole portion 38c-2. The lower guide hole portion 38c-2 has an inner diameter slightly greater than the outer diameter of the distal end of the specimen injector so that the movement of the distal portion 6 is limited to prevent the distal portion 6 from projecting into the specimen injection port 3. With the aforesaid construction of the guide hole 38c, the distal portion 6 of the specimen injector is guided into the lower guide hole portion 38c-2 by the upper guide hole portion 38c-1, and positioned by the lower guide hole portion 38c-2. The guide portions 38a each have a stepped lower end, which is fitted in the specimen injection port 3. Further, the guide portions 38a each have a flange provided on an upper end thereof.

The aforesaid arrangement makes it possible to properly inject the liquid specimen into the channel 4 without leakage, and prevents displacement of the distal portion 6 of the specimen injector from the guide hole 38c during the injection of the specimen.

As a result, the possibility that the operator touches the specimen can assuredly be eliminated, thereby preventing the infection of the operator.

According to the present invention, the liquid specimen analysis disk assemblies include at least one of the guide member having the guide holes for guiding the distal portion of the specimen injector toward the specimen injection ports, the cover member for opening and closing the guide holes and the seal member for sealing the specimen injection ports. This improves the handling ease when the liquid specimen which may possibly contain an infectious pathogen is injected into the disk, and prevents the specimen from leaking out of the disk and adhering onto the outer surface of the disk. Thus, the operator can safely perform the analytic operation without touching the specimen.

What is claimed is:

1. A liquid specimen analysis disk assembly comprising:
   a liquid specimen analysis disk to be optically scanned for analyzing a liquid specimen therein, the liquid specimen analysis disk having a specimen injection port for injecting the liquid specimen into a specimen spreading cavity in which the liquid specimen is spread by rotating the disk about an axis of the disk; and
   a guide member detachably provided on the disk and having a guide hole for guiding a distal portion of a specimen injector toward the specimen injection port for the injection of the liquid specimen.

2. The liquid specimen analysis disk assembly as set forth in claim 1, wherein the guide hole of the guide member is tapered so that one end opening thereof opposed to the specimen injection port has a smaller diameter than the other end opening thereof facing away from the specimen injection port.

3. The liquid specimen analysis disk assembly as set forth in claim 1, wherein the guide hole of the guide member has an inner diameter such as to be fitted around a part of the distal portion of the specimen injector.

4. The liquid specimen analysis disk assembly as set forth in claim 1, wherein one end opening of the guide hole opposed to the specimen injection port has a smaller inner diameter than the specimen injection port.

5. The liquid specimen analysis disk assembly as set forth in claim 1, wherein the guide member has a tubular projection surrounding one end opening of the guide hole opposed to the specimen injection port.

6. The liquid specimen analysis disk assembly as set forth in claim 5, wherein the tubular projection has a distal end having an outer diameter smaller than the inner diameter of the specimen injection port.

7. The liquid specimen analysis disk assembly as set forth in claim 1, wherein the guide member is constituted by a lid of a disk case.

8. The liquid specimen analysis disk assembly as set forth in claim 1, further comprising a cover member provided on the guide member for opening and closing the guide hole.

9. The liquid specimen analysis disk assembly as set forth in claim 8, wherein the cover member is pivotal parallel to the surface of the disk about a pivot axis on the lid of the disk case.

10. The liquid specimen analysis disk assembly as set forth in claim 9, wherein the cover member has an engagement member which is brought into engagement with an engagement member provided on the lid of the disk case, when the cover member is pivoted to cover the specimen injection port, to prevent the cover member from pivoting in a reverse direction.

11. The liquid specimen analysis disk assembly as set forth in claim 7, further comprising an adhesive sealing sheet which is retained in a folded state or in a rolled state between the disk and the lid of the disk case and extended for sealing the specimen injection port, and a tab provided integrally with the adhesive sealing sheet as extending out of the disk case.

12. The liquid specimen analysis disk assembly as set forth in claim 11, wherein the tab is constituted by a part of a releasable sheet which lines the adhesive sealing sheet.

13. The liquid specimen analysis disk assembly as set forth in claim 11, further comprising a roller member coupled with the tab for pressing the extended adhesive sealing sheet against the disk surface.

14. The liquid specimen analysis disk assembly as set forth in claim 11, wherein the lid is overlapped with a case body of the disk case, and the lid and the case body each have an opening formed in an overlapped portion thereof for extracting the tab out of the disk case.

15. A liquid specimen analysis disk assembly comprising:
    a liquid specimen analysis disk to be optically scanned for analyzing a liquid specimen therein, the liquid specimen analysis disk having a specimen injection port for injecting the liquid specimen into a specimen spreading cavity in which the liquid specimen is spread by rotating the disk about an axis of the disk, the liquid specimen analysis disk having a groove formed in the surface of the disk provided with the specimen injection port; and
    a seal member slidable in engagement with the groove for sealing the specimen injection port.

16. The liquid specimen analysis disk assembly as set forth in claim 15, wherein the seal member and the groove respectively have engagement members which are brought into engagement with each other, when the seal member is slid to seal the specimen injection port, to prevent the seal member from sliding in a reverse direction.

17. A liquid specimen analysis disk assembly comprising:
    a liquid specimen analysis disk to be optically scanned for analyzing liquid specimens therein, the liquid specimen analysis disk having a plurality of specimen injection ports for injecting the liquid specimens into specimen spreading cavities in which the liquid specimens are respectively spread by rotating the disk about an axis of the disk; and
    a temporary seal retaining member detachably provided on the disk and having plural adhesive sealing sheets temporarily retained at predetermined positions thereon, the adhesive sealing sheets being each covered with a releasable sheet.

18. The liquid specimen analysis disk assembly as set forth in claim 17, wherein the temporary seal retaining member is partly or entirely composed of a resilient material.

19. The liquid specimen analysis disk assembly as set forth in claim 17, wherein first identification marks having different characters are provided in association with the respective specimen injection ports, and second identification marks having characters corresponding to the characters of the first identification marks are respectively provided on the adhesive sealing sheets or the releasable sheets associated with the respective specimen injection ports, or on the temporary seal retaining member in the vicinity of the respective adhesive sealing sheets.

20. The liquid specimen analysis disk assembly as set forth in claim 17, wherein the temporary seal retaining member is pivotal about a pivot axis of a hinge provided in a disk case.

21. The liquid specimen analysis disk assembly as set forth in claim 20, wherein the temporary seal retaining member is constituted by a lid of the disk case.

22. A liquid specimen analysis disk assembly comprising:
a liquid specimen analysis disk to be optically scanned for analyzing liquid specimens therein, the liquid specimen analysis disk having a plurality of specimen injection ports for injecting the liquid specimens into specimen spreading cavities in which the liquid specimens are respectively spread by rotating the disk about an axis of the disk; and
a guide member having plural introduction members provided in association with the respective specimen injection ports and linked to one another, the introduction members each having a guide hole for guiding a distal portion of a specimen injector toward the specimen injection port for the injection of the liquid specimen.

23. The liquid specimen analysis disk assembly as set forth in claim 22, wherein the introduction members each have a truncated cone shape, and the guide hole includes an upper guide hole portion and a lower guide hole portion for guiding the distal portion of the specimen injector.

* * * * *